(12) United States Patent
Ou et al.

(10) Patent No.: US 9,725,378 B2
(45) Date of Patent: Aug. 8, 2017

(54) PARAXYLENE SEPARATION PROCESS

(71) Applicant: ExxonMobil Chemical Patents Inc., Baytown, TX (US)

(72) Inventors: John D. Ou, Houston, TX (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 149 days.

(21) Appl. No.: 14/624,861

(22) Filed: Feb. 18, 2015

(65) Prior Publication Data

US 2015/0266794 A1   Sep. 24, 2015

Related U.S. Application Data

(60) Provisional application No. 61/955,907, filed on Mar. 20, 2014.

(30) Foreign Application Priority Data

May 12, 2014   (EP) ..................................... 14167834

(51) Int. Cl.
| | | |
|---|---|---|
| C07C 5/27 | (2006.01) |
| C07C 6/12 | (2006.01) |
| C07C 5/22 | (2006.01) |
| C07C 4/02 | (2006.01) |
| C07C 6/06 | (2006.01) |
| C07C 7/12 | (2006.01) |

(52) U.S. Cl.
CPC ................ *C07C 5/222* (2013.01); *C07C 4/02* (2013.01); *C07C 5/277* (2013.01); *C07C 6/06* (2013.01); *C07C 7/12* (2013.01); C07C 2529/40 (2013.01)

(58) Field of Classification Search
CPC .................................... C07C 6/12; C07C 5/27
USPC ................ 585/319, 304, 300, 477, 478, 470
See application file for complete search history.

(56) References Cited

U.S. PATENT DOCUMENTS

| | | |
|---|---|---|
| 2,985,589 A | 5/1961 | Broughton et al. |
| 3,310,486 A | 3/1967 | Broughton et al. |
| (Continued) | | |

FOREIGN PATENT DOCUMENTS

FR        2792632        10/2000

*Primary Examiner* — Thuan D Dang

(57) ABSTRACT

The invention relates to a p-xylene separation process wherein at least a portion of ethylbenzene present in an aromatics-containing feed is removed prior to isomerization. Aspects of the invention provide a process for producing p-xylene. The process includes providing a first mixture comprising ≥5.0 wt. % of aromatic $C_8$ isomers, the $C_8$ isomers comprising p-xylene and ethylbenzene. A p-xylene-containing portion and an ethylbenzene-containing portion are separated from the first mixture in a first separation stage to form a p-xylene-depleted raffinate. The first separation stage can include at least one simulated moving-bed adsorptive separation stage. At least a portion the p-xylene-depleted raffinate in the liquid phase is reacted to produce a reactor effluent comprising aromatic $C_8$ isomers. The first mixture can be combined with ≥50.0 wt. % of the reactor effluent's aromatic $C_8$ isomers. The combining can be carried out before and/or during the separating of the p-xylene and ethylbenzene portions.

11 Claims, 3 Drawing Sheets

(56) References Cited

U.S. PATENT DOCUMENTS

| | | | |
|---|---|---|---|
| 3,662,020 A | 5/1972 | Hemminger et al. | |
| 3,856,874 A * | 12/1974 | Hayward | C07C 5/2708 |
| | | | 585/302 |
| 5,012,038 A | 4/1991 | Zinnen | |
| 5,629,467 A | 5/1997 | Hotier et al. | |
| 7,626,065 B2 | 12/2009 | Ou et al. | |
| 7,915,471 B2 | 3/2011 | Leflaive et al. | |
| 2002/0065444 A1 * | 5/2002 | Deckman | C07C 5/2708 |
| | | | 585/477 |
| 2004/0220439 A1 | 11/2004 | Williams et al. | |
| 2012/0108868 A1 * | 5/2012 | Pilliod | C07C 5/2732 |
| | | | 585/300 |

* cited by examiner

PARAXYLENE SEPARATION PROCESS

PRIORITY

This application claims priority to U.S. patent Application No. 61/955,907, filed Mar. 20, 2014, and EP 14167834.2 filed May 12, 2014, the disclosures of which are incorporated in their entireties.

FIELD OF INVENTION

Aspects of the invention relate to para-xylene (p-xylene) separation processes. In particular, aspects of the invention relate to xylene loop processes.

BACKGROUND OF INVENTION

Aromatic hydrocarbons, such as benzene, toluene, xylene, etc. are useful as fuels, solvents, and as feeds for various chemical processes. Of the xylenes, para-xylene is particularly useful for manufacturing phthalic acids such as terephthalic acid, which is an intermediate in the manufacture of synthetic fibers such as polyester fibers. Xylenes can be produced from naphtha, e.g., by catalytic reforming, with the reformate product containing a mixture of xylene isomers and ethylbenzene. Separating p-xylene from the mixture generally requires stringent separations, e.g., separations utilizing superfractionation and multistage refrigeration steps. Such separations are characterized by complexity, high energy-usage, and high cost.

Chromatographic separation is an alternative to more stringent separations, such as superfractionation, for removing p-xylene from a mixture of aromatic $C_8$ isomers. Chromatographic separation involves simulating a moving bed of selective adsorbent. Examples of commercial processes in which p-xylene is separated from aromatic $C_8$ isomers by simulated moving-bed separation include PAREX, available from UOP, ELUXYL, available from Axens, and ARO-MAX, available from Toray. Although a raffinate depleted in p-xylene can be recycled as a feed component to the p-xylene separation step, ethylbenzene will undesirably accumulate in the recycle stream.

In order to overcome this difficulty, p-xylene is conventionally produced in a continuous process (commonly referred to as a xylene loop), in which p-xylene-depleted raffinate is isomerized to reduce the amount of ethylbenzene therein. The isomerization reduces the amount of ethylbenzene in the stream by converting it into an equilibrium or near-equilibrium xylene mixture, e.g., a mixture comprising xylene isomers; diethylbenzene; benzene; and non-aromatics such as $C_2$-$C_6$ olefins and $C_1$-$C_6$ paraffins. One such process involves (a) providing a mixture of aromatic $C_8$ isomers containing p-xylene, (b) separating from the $C_8$ isomers a high-purity p-xylene extract and a p-xylene-depleted raffinate by simulated moving bed adsorption, crystallization, or a combination thereof, (c) catalytically isomerizing the p-xylene-depleted raffinate to produce an isomerate, and (e) recycling the isomerate to step (a).

Vapor-phase isomerization of the raffinate's ethylbenzene is generally needed to achieve an ethylbenzene content of ≤10.0 mole % ethylbenzene per mole of isomerate. However, vapor-phase isomerization has many disadvantages, including high energy consumption, costly and complex process equipment, and high xylenes loss due to conversion of the xylenes in the raffinate into undesirable products such as light gases and heavy aromatics, e.g., by one or more side-reactions such as one or more of cracking, transalkylation, or disproportionation. Attempts to overcome these disadvantages include reducing the quantity of raffinate going to the vapor-phase isomerization, e.g., removing ethylbenzene from the raffinate by (i) superfractionation, as disclosed in French Patent FR-A-2792632, or (ii) using chromatographic ethylbenzene separation in the p-xylene separation stage, as disclosed in U.S. Pat. No. 7,915,471. The separated ethylbenzene is isomerized in a vapor-phase isomerization stage, with the remainder of the raffinate being isomerized in a liquid-phase isomerization stage. The liquid-phase isomerization stage is operated under conditions which lessen undesired cracking, transalkylation, and disproportionation side-reactions. Isomerates from the vapor-phase and liquid-phase isomerization stages are then combined and recycled to stage (a) of the xylene loop.

Even when ethylbenzene is separated for vapor-phase isomerization, with the remainder of the p-xylene-depleted raffinate subjected to liquid-phase isomerization, the vapor-phase isomerization stage contributes to xylene-loop inefficiencies. Some of these inefficiencies result from one or more of (i) the need to vaporize the separated ethylbenzene and then re-condense the vapor-phase isomerate for combining with the isomerate derived from the liquid-phase isomerization stage, (ii) the need to separate unreacted molecular hydrogen vapor for re-use as an isomerization treat gas, and (iii) the need for removing non-aromatics formed during isomerization. Consequently, it is desired to further lessen or even eliminate the need for vapor-phase isomerization.

SUMMARY OF INVENTION

It has been found that xylene loop efficiency is unexpectedly improved by separating and removing from the loop at least a portion of the ethylbenzene present in the feed to the p-xylene separation stage and/or at least a portion of the non-aromatics present in the feed to the p-xylene separation stage, the ethylbenzene and/or non-aromatics removal being carried out upstream of raffinate isomerization. Separating and conducting away from the xylene loop at least a portion of the ethylbenzene increases xylene loop energy efficiency, e.g., by lessening the number of Joules consumed by the xylene loop to produce one kilogram of p-xylene by ≥20%, e.g., ≥25% when ≥90 wt. % of ethylbenzene present in the feed to the p-xylene separation stage is removed upstream of the isomerization. Moreover, removing at least a portion of the xylene loop's ethylbenzene decreases the xylene loop's complexity, e.g., by lessening or even eliminating the need for an energy-intensive and complex vapor-phase isomerization downstream of p-xylene separation. The ethylbenzene can be removed in the p-xylene separation stage, e.g., as a component of a second raffinate that is chromatographically separated in the p-xylene separation stage. It is also advantageous to remove at least a portion of any non-aromatics from the xylene loop, e.g., removing non-aromatics upstream of raffinate isomerization. The advantages can be attained even in aspects where ethylbenzene is not removed. Certain advantages result from the relatively high-value of gasoline boiling-range non-aromatics (e.g., those having an atmospheric-pressure boiling point in the range of from 30° F. to 430° F.), which can be removed from the loop for use in higher-value uses, e.g., as a blendstock for transportation fuels. Removing non-aromatics is also advantageous because doing so lessens the amount of hydrogen utilized in the process, and the associated compression costs.

In certain aspects, the invention relates to a process for producing p-xylene, the process comprising, (a) providing a first mixture comprising ≥5.0 wt. % of aromatic $C_8$ isomers, based on the weight of the first mixture, said aromatic $C_8$ isomers comprising p-xylene and ethylbenzene; (b) separating a p-xylene-containing portion and an ethylbenzene-containing portion from the first mixture in a first separation stage to form a p-xylene-depleted raffinate, wherein the first separation stage optionally includes at least one simulated moving-bed adsorptive separation stage; (c) reacting at least a portion the p-xylene-depleted raffinate in the liquid phase to produce a reactor effluent comprising aromatic $C_8$ isomers; and (d) combining with the first mixture ≥50.0 wt. %, preferably ≥90.0 wt. %, of the reactor effluent's aromatic $C_8$ isomers, preferably p-xylene, based on the weight of the reactor effluent's aromatic $C_8$ isomers, the combining being carried out before and/or during the separating of (b). At least part of the separated ethylbenzene-containing portion is conducted away.

A particular aspect relates to a process for producing p-xylene, the process comprising providing a first mixture comprising ≥5.0 wt. % of aromatic $C_8$ isomers, based on the weight of the first mixture, said $C_8$ isomers comprising p-xylene and ethylbenzene. The following components of the first mixture are separated in a first separation stage: (i) a p-xylene-depleted raffinate; (ii) a p-xylene-containing portion comprising ≥10.0 wt. % of the first mixture's p-xylene, based on the weight of the first mixture's p-xylene; and (iii) an ethylbenzene-containing portion comprising ≥10.0 wt. % of the first mixture's ethylbenzene, based on the weight of the first mixture's ethylbenzene. At least a portion of the p-xylene-containing portion is conducted away from the process, as is ≥50.0 wt. % of the ethylbenzene-containing portion, based on the weight of the ethylbenzene-containing portion. The process continues by isomerizing at least a portion the p-xylene-depleted raffinate in the liquid phase wherein ≤10.0 wt. %, e.g., ≤1.0 wt. % or ≤0.1 wt. %, of the p-xylene-depleted raffinate is in the vapor phase during the isomerizing, the weight percent being based on the weight of the p-xylene-depleted raffinate. The isomerizing produces a reactor effluent comprising ≥90.0 wt. % p-xylene, based on the weight of the reactor effluent's aromatic $C_8$ isomers. At least a portion of the reactor effluent is combined with the first mixture, the combining being carried out before and/or during the separating in the first separation stage.

In other aspects, the invention relates to an improved xylene loop, wherein the xylene loop comprises (a) providing a first mixture comprising aromatic $C_8$ isomers; (b) separating from the first mixture in a first stage: (i) a p-xylene-depleted raffinate; (ii) a p-xylene-containing portion comprising ≥10.0 wt. % of the mixture's p-xylene, based on the weight of the mixture's p-xylene; and (iii) an ethylbenzene-containing portion comprising ≥10.0 wt. % of the mixture's ethylbenzene, based on the weight of the mixture's ethylbenzene; wherein the first separation stage includes at least one simulated moving-bed adsorption chromatographic separation; (c) conducting away at least a portion of the separated p-xylene; (d) reacting at least a portion the p-xylene-depleted raffinate in the liquid phase to produce a reactor effluent comprising aromatic $C_8$ isomers; and (e) recycling to step (b) ≥50.0 wt. % of aromatic $C_8$ isomers of the reactor effluent, based on the weight of the aromatic $C_8$ isomers in the reactor effluent. The improvement comprises: (f) conducting away from the xylene loop ≥50.0 wt. % of the ethylbenzene separated in step (c), based on the weight of the separated ethylbenzene; and (g) exposing ≤10.0 wt. % of aromatic $C_8$ isomers in the xylene loop to vapor-phase isomerization, based on the weight of aromatic $C_8$ isomers in the xylene loop.

DETAILED DESCRIPTION

Figure 1:
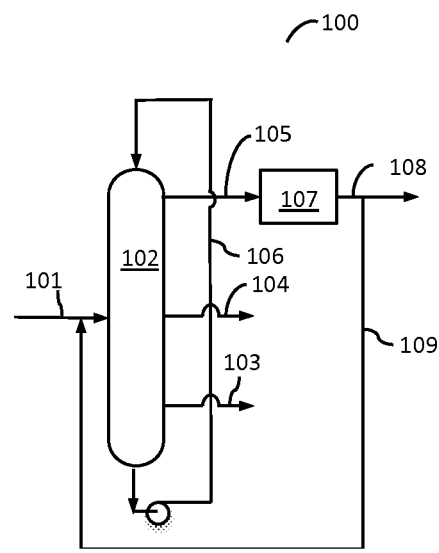
FIG. 1 illustrates a p-xylene separation process according to an aspect of the invention.

The following description relates to aspects of the invention which include removing ethylbenzene from a xylene loop upstream of isomerization. The invention is not limited to these aspects, and is not meant to foreclose other aspects within the broader scope of the invention, such as those which include non-aromatics separation. FIG. 1 schematically illustrates a process 100 which features certain aspects of the invention. First mixture 101 is passed to first separation stage 102 where a p-xylene-containing portion 103 and an ethylbenzene-containing portion 104 are separated and conducted away, in order to produce a p-xylene-depleted raffinate 105 for the isomerization. First mixture 101 typically comprises ≥5.0 wt. % of aromatic $C_8$ isomers, based on the weight of the first mixture, said aromatic $C_8$ isomers comprising p-xylene and ethylbenzene. Generally, the content of aromatic $C_8$ isomers in first mixture 101 may range from 5.0 to 100.0 wt. %. The lower limit on the content of aromatic $C_8$ isomers in first mixture 101 may be 5.0 wt. %, 10.0 wt. %, 20.0 wt. %, 30.0 wt. %, 40.0 wt. %, 50.0 wt. %, 60.0 wt. %, 70.0 wt. %, 80.0 wt. %, 90.0 wt. %, 95.0 wt. %, 99.0 wt. %, or 100.0 wt. %. The upper limit on the content of aromatic $C_8$ isomers in first mixture 101 may be 5.0 wt. %, 10.0 wt. %, 20.0 wt. %, 30.0 wt. %, 40.0 wt. %, 50.0 wt. %, 60.0 wt. %, 70.0 wt. %, 80.0 wt. %, 90.0 wt. %, 95.0 wt. %, 99.0 wt. %, or 100.0 wt. %. Aspects expressly described herein include those where any lower limit is combined with any upper limit. In particular aspects, first mixture 101 comprises ≥50.0 wt. %. e.g., ≥60.0 wt. %, ≥65.0 wt. %, ≥70.0 wt. %, ≥75.0 wt. %, ≥80.0 wt. %, ≥85.0 wt. %, ≥90.0 wt. %, 95.0 wt. %, ≥99.0 wt. %, of a mixture of p-xylene, ethylbenzene, meta-xylene (m-xylene), and ortho-xylene (o-xylene), based on the weight of the first mixture 101.

The first separation stage 102 is typically a simulated moving bed absorptive separation unit having solvent (sometimes referred to as "desorbant") circulating therethrough via line 106. The circulation can be carried out using one or more pumps, such as the pump shown schematically in FIG. 1 as a component of stage 102. In particular aspects the first separation stage 102 is a chromatographic separation stage. Solvent 106 should be selected to separate under the separation conditions, e.g., solvent flow, temperature, etc., the components of first mixture 101 as desired. Typical solvents include hydrocarbon solvents, e.g., toluene. Exemplary separation processes are described in U.S. Pat. No. 7,915,471, incorporated herein by reference in its entirety.

Separation stage 102 should be operated such that p-xylene-containing portion 103 comprises ≥10.0 wt. % of the first mixture's p-xylene, based on the weight of the first mixture's p-xylene. Generally, the content of p-xylene in p-xylene-containing portion 103 may range from 10.0 to 100.0 wt. % of the first mixture's p-xylene. The lower limit on the content of p-xylene in the p-xylene-containing portion 103 may be 10.0 wt. %, 20.0 wt. %, 30.0 wt. %, 40.0 wt. %, 50.0 wt. %, 60.0 wt. %, 70.0 wt. %, 80.0 wt. %, 90.0 wt. %, 95.0 wt. %, 99.0 wt. %, or 100.0 wt. %. The upper limit on the content of p-xylene in p-xylene-containing portion 103 may be 10.0 wt. %, 20.0 wt. %, 30.0 wt. %, 40.0 wt. %, 50.0 wt. %, 60.0 wt. %, 70.0 wt. %, 80.0 wt. %, 90.0 wt. %, 95.0 wt. %, 99.0 wt. %, or 100.0 wt. %. Aspects expressly described herein include those where any lower limit is combined with any upper limit. In particular aspects, p-xylene-containing portion 103 comprises 10.0 to 75.0 wt. %, 10.0 to 65.0 wt. %, 10.0 to 50.0 wt. %, 10.0 to 40.0 wt. %, 10.0 to 30.0 wt. %, or 10.0 to 20.0 wt. % of the first mixture's p-xylene. In some aspects, p-xylene-containing portion 103 comprises 20.0 to 75.0 wt. %, 30.0 to 75 wt. %, 40.0 to 75 wt. %, 50.0 to 75.0 wt. %, or 65.0 to 75.0 wt. % of the first mixture's p-xylene. In particular aspects, least a portion of the p-xylene-containing portion 103 is conducted away from the process 100. In certain aspects, 10.0 to 100.0 wt. %, e.g., 40.0 to 100.0 wt. %, 50.0 to 100.0 wt. %, 60.0 to 100.0 wt. %, 70.0 to 100.0 wt. %, 80.0 to 100.0 wt. %, 80.0 to 100.0 wt. %, or 95.0 to 100.0 wt. %, of the p-xylene portion is conducted away from the process.

Ethylbenzene is separated and removed from process 100 via ethylbenzene-containing portion 104, which typically comprises comprising ≥10.0 wt. % of the first mixture's ethylbenzene, based on the weight of the first mixture's ethylbenzene. The lower limit on the content of ethylbenzene in the ethylbenzene-containing portion 104 may be 10.0 wt. %, 20.0 wt. %, 30.0 wt. %, 40.0 wt. %, 50.0 wt. %, 60.0 wt. %, 70.0 wt. %, 80.0 wt. %, 90.0 wt. %, 95.0 wt. %, 99.0 wt. %, or 100.0 wt. %. The upper limit on the content of ethylbenzene in ethylbenzene-containing portion 104 may be 10.0 wt. %, 20.0 wt. %, 30.0 wt. %, 40.0 wt. %, 50.0 wt. %, 60.0 wt. %, 70.0 wt. %, 80.0 wt. %, 90.0 wt. %, 95.0 wt. %, 99.0 wt. %, or 100.0 wt. %. Aspects expressly described herein include those where any lower limit is combined with any upper limit. Generally, ethylbenzene-containing portion 104 comprises 10.0 to 75.0 wt. %, 10.0 to 65.0 wt. %, 10.0 to 50.0 wt. %, 10.0 to 40.0 wt. %, 10.0 to 30.0 wt. %, or 10.0 to 20.0 wt. % of the first mixture's ethylbenzene. In certain aspects, ethylbenzene-containing portion 104 comprises 20.0 to 75.0 wt. %, 30.0 to 75.0 wt. %, 40.0 to 75 wt. %, 50.0 to 75.0 wt. %, or 65.0 to 75.0 wt. % of the first mixture's p-xylene. Removing at least a portion of the ethylbenzene from the process decreases the xylene loop's complexity, e.g., by lessening or even eliminating the need for an energy-intensive and complex vapor-phase isomerization downstream of p-xylene separation. The ethylbenzene can be removed in the p-xylene separation stage, e.g., as a component of a second extract. The second extract can be chromatographically separated in the p-xylene separation stage, as disclosed in U.S. Pat. No. 7,915,471. In particular aspects, at least a portion of the ethylbenzene-containing portion 104 is conducted away from the process 100, e.g., ≥10.0 wt. % of the ethylbenzene-containing portion is conducted away, based on the weight of the ethylbenzene-containing portion. In certain aspects, 10.0 to 100.0 wt. %, e.g., 40.0 to 100.0 wt. %, 50.0 to 100.0 wt. %, 60.0 to 100.0 wt. %, 70.0 to 100.0 wt. %, 80.0 to 100.0 wt. %, 80.0 to 100.0 wt. %, or 95.0 to 100.0 wt. %, of ethylbenzene-containing portion 104 is conducted away from the process. Since at least part of the first mixture's ethylbenzene is separated and conducted away, the process generally includes isomerizing <90.0 wt. % of the first mixture's ethylbenzene, e.g., ≤50.0 wt. %, such as ≤25.0 wt. %. In certain aspects, the process includes isomerizing ≤10.0 wt. % of the first mixture's ethylbenzene, e.g., ≤5.0 wt. %, such as ≤1.0 wt. ≤1.0 wt. %.

The process may include separating at least a portion of any non-aromatic hydrocarbon molecules from the first mixture 101. This can be done upstream of stage 107, e.g., in stage 102 (not shown). First separation stage 102 may remove from 5.0 to 100 wt. % of any non-aromatic hydrocarbons, based on the amount of such hydrocarbons in the first mixture. In particular aspects, the first separation stage 102 removes ≥50.0 wt. %, preferably ≥75.0 wt. %, or ≥90.0 wt. % of the non-aromatic hydrocarbons. Certain non-aromatic hydrocarbon molecules, e.g., $C_9$ non-aromatic molecules, have approximately the same volatility as p-xylene. It is conventional to ameliorate problems associated with non-aromatics separation from the xylene loop by cracking at least a portion of the non-aromatics during xylene isomerization. This approach lessens xylene loop efficiency (as a result of, e.g., bottlenecking of the isomerization stage), and leads to an increase in separation complexity as a result of the need to remove the cracked products. It has been found that this difficulty can be overcome by removing at least a portion of the non-aromatics upstream of the isomerization, e.g., by removing non-aromatics from the first mixture in the first separation stage. As in the case of ethylbenzene removal, separation of non-aromatics can be carried out using at least one simulated moving-bed adsorption chromatographic separation. Advantageously, non-aromatics separation and ethylbenzene separation can be carried out in the same simulated moving-bed adsorption chromatographic separation using the same desorbent. The chromatographic separation can be carried out using conventional methods, such as those described in U.S. Pat. No. 3,662,020, which is incorporated by reference herein in its entirety. One or more conventional desorbents can be used, e.g., toluene. Conventional configurations can be utilized for the simulated moving-bed adsorption chromatographic separation of the first separation stage, e.g., stacked-bed mode and/or multiple bed mode. Suitable configurations are disclosed in U.S. Pat. Nos. 2,985,589 and 3,310,486, which are incorporated by reference herein in their entirety. In certain aspects, four streams are conducted away from the first separation stage: (i) first and second extracts and (ii) first and second raffinates. Referring again to FIG. 1, the first extract corresponds to the p-xylene-containing portion removed from stage 102. The second extract corresponds to the ethylbenzene portion removed from stage 102. The first raffinate comprises at least a portion of the first mixture's m-xylene and o-xylene, e.g., ≥50.0 wt. % of the first mixture's m-xylene and ≥50.0 wt. % of the first mixture's o-xylene. The second raffinate comprises non-aromatics, e.g., ≥50.0 wt. % of the first mixture's non-aromatics. Although it is not required, the invention is compatible with removing at least a portion of any desorbent from one or more of the first extract, second extract, first raffinate, and second raffinate. For example, desorbent can be removed from the first raffinate upstream of the isomerization in order to further debottleneck the isomerizing. Since at least part of the first mixture's non-aromatics can be separated and conducted away, the process optionally includes subjecting to isomerization conditions <90.0 wt. % of the first mixture's non-aromatics, e.g., ≤50.0 wt. %, such as ≤25.0 wt. %. In certain aspects, the process includes subjecting ≤10.0 wt. % of the first mixture's non-aromatics to isomerization conditions, ≤5.0 wt. %, such as ≤1.0 wt. %.

The p-xylene-depleted raffinate 105 is provided to reactor 107 where raffinate 105 is reacted in the liquid phase to produce a reactor effluent comprising aromatic $C_8$ isomers. Reactor 107 may be any type of reactor or reactor process suitable for increasing the amount of $C_8$ isomers, relative to the amount of aromatic $C_8$ isomers in raffinate 105. Reactor 107 typically performs at least one of (i) one or more reforming reactions, (ii) one or more disproportionation reactions, (iii) one or more transalkylation reactions, and (iv) one or more cracking reactions. While the reaction processes in reactor 107 are conducted in the liquid phase, some of raffinate 105 may be in the vapor phase. Thus, in particular aspects, ≤10.0 wt. %, e.g., ≤7.5 wt. %, ≤5.0 wt. %, ≤2.5 wt. %, ≤1.0 wt. %, ≤0.5 wt. %, −0.2 wt. %, ≤0.1 wt. %, of the p-xylene-depleted raffinate 105 in reactor 107 is in the vapor phase during the reacting, the weight percent being based on the weight of the p-xylene-depleted raffinate 105.

Reactor effluent 108 generally comprises products formed in reactor 107, and can also include unreacted raffinate. For example, reactor effluent 108 can comprise $C_1$-$C_7$ compounds, $C_8$ aromatic isomers, and $C_{9+}$ aromatics. In certain aspects, the concentration of p-xylene in effluent 108 may be suitable for use in other processes or it may be sent for further purification and/or isolation of the p-xylene. In certain aspects, at least a portion of the reactor effluent 108 is recycled through line 109 to be combined with the first mixture 101. Any desirable amount of reactor effluent may be recycled through line 109. Typically, ≥50.0 wt. %, of the aromatic $C_8$ isomers of the reactor effluent 108, based on the total amount of aromatic $C_8$ isomers in reactor effluent 108, are recycled for combining with the first mixture 101. The lower limit on the amount of aromatic $C_8$ isomers recycled for combining with the first mixture 101 may be 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, or 100.0 wt. %. The upper limit on the amount of aromatic $C_8$ isomers recycled for combining with the first mixture 101 may be 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, or 100.0 wt. %. Any combination of lower and upper limits on the amount of aromatic $C_8$ isomers recycled for combining with the first mixture 101 is expressed disclosed. In particular aspects, the aromatic $C_8$ isomers recycled through line 109 comprise ≥50.0 wt. % (e.g., ≥50.0 wt. %, ≥55.0 wt. %, ≥60.0 wt. %, ≥65.0 wt. %, ≥70.0 wt. %, ≥75.0 wt. %, ≥80.0 wt. %, ≥85.0 wt. %, ≥90.0 wt. %, ≥95.0 wt. %, ≥99.0 wt. %, xylene isomers (e.g., o-xylene, m-xylene, p-xylene). In particular aspects, the xylene isomers comprise ≥50.0 wt. %, ≥55.0 wt. %, ≥60.0 wt. %, ≥65.0 wt. %, ≥70.0 wt. %, ≥75.0 wt. %, ≥80.0 wt. %, ≥85.0 wt. %, ≥90.0 wt. %, ≥95.0 wt. %, ≥99.0 wt. %, p-xylene. Line 109 typically provides the aromatic $C_8$ isomers before and/or during the separating of (b).

Figure 2:
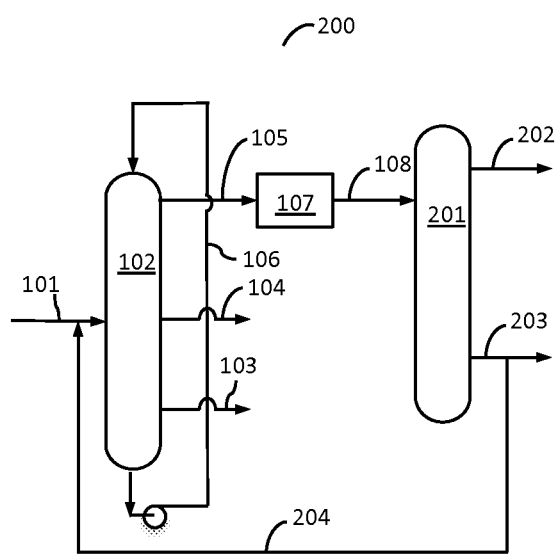
FIG. 2 illustrates a p-xylene separation process according to aspects of the invention including a second separation stage wherein at least a portion of any $C_1$-$C_7$ compounds are removed from the reactor effluent.

With continuing reference to FIG. 1, FIG. 2 illustrates process 200. Process 200 includes providing the reactor effluent 108 to a second separation stage 201 wherein at least a portion of one or more $C_1$-$C_7$ compounds in the reactor effluent 108 are separated via line 202. Particular aspects of process 200 include conducting the separated one or more $C_1$-$C_7$ compounds away from the process. Heavier compounds, including aromatic $C_8$ isomers and $C_{9+}$ hydrocarbons, exit second separation stage 201 via line 203. Separation stage 201 may be any separation means suitable for separating $C_1$-$C_7$ compounds from $C_{8+}$ hydrocarbons. In particular aspects, separation stage 201 is a stabilization column or distillation column. Typically, the $C_1$-$C_7$ compounds are separated in separation stage 201 before the reactor effluent 108 is recycled for combining with the first mixture 101, as shown in FIG. 2. In other words, the $C_1$-$C_7$ compounds are separated and at least a portion of the $C_{8+}$ hydrocarbons of line 203 are recycled through line 204 to be combined with first mixture 101. Any desirable amount of the $C_{8+}$ hydrocarbons exiting separation stage 201 via line 203 may be recycled through line 204. Typically, ≥50.0 wt. %, of the $C_{8+}$ hydrocarbons of the separation stage 201, based on the total amount of $C_{8+}$ hydrocarbons exiting separation stage 201, are recycled for combining with the first mixture 101. The lower limit on the amount of $C_{8+}$ hydrocarbons recycled for combining with the first mixture 101 may be 10.0 wt. %, 20.0 wt. %, 30.0 wt. %, 40.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, or 100.0 wt. %. The upper limit on the amount of $C_{8+}$ hydrocarbons recycled for combining with the first mixture 101 may be 10.0 wt. %, 20.0 wt. %, 30.0 wt. %, 40.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, or 100.0 wt. %. Any combination of lower and upper limits on the amount of $C_{8+}$ hydrocarbons recycled for combining with the first mixture 101 is expressed disclosed. In particular aspects, the $C_{8+}$ hydrocarbons recycled through line 204 comprise ≥50.0 wt. % (e.g., ≥50.0 wt. %, ≥55.0 wt. %, ≥60.0 wt. %, ≥65.0 wt. %, ≥70.0 wt. %, ≥75.0 wt. %, ≥80.0 wt. %, ≥85.0 wt. %, ≥90.0 wt. %, ≥95.0 wt. %, ≥99.0 wt. %), $C_{8+}$ aromatic hydrocarbons (e.g., ethylbenzene, o-xylene, m-xylene, p-xylene). In particular aspects, the aromatic $C_{8+}$ hydrocarbons recycled via line 204 comprise ≥50.0 wt. %, ≥55.0 wt. %, ≥60.0 wt. %, ≥65.0 wt. %, ≥70.0 wt. %, ≥75.0 wt. %, ≥80.0 wt. %, ≥85.0 wt. %, ≥90.0 wt. %, ≥95.0 wt. %, ≥99.0 wt. %, p-xylene.

Figure 3:
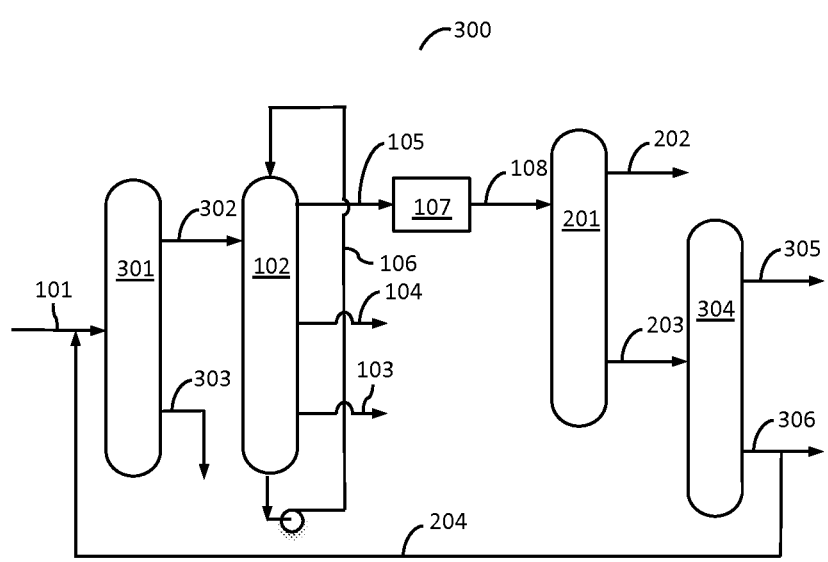
FIG. 3 illustrates a p-xylene separation process according to aspects of the invention. The separation process includes removing one or more by-products from the first mixture and/or providing the $C_{8+}$ hydrocarbons to a third separation stage 301.

With continuing reference to FIGS. 1 and 2, FIG. 3 illustrates an exemplary process 300. Optionally, process 100 or process 200 may include removing one or more by-products from the first mixture and/or providing at least a portion of any $C_{8+}$ hydrocarbons exiting the separation stage 201 to a third separation stage 301 via line 203. Optionally, the portion of $C_{8+}$ hydrocarbon can be derived from a fourth separation stage 304. Stage 304 can be located downstream of stage 201, as shown in the figure. For example, in process 300, first mixture 101 may be passed to third separation stage 301, wherein at least a portion of a by-product, e.g., o-xylene and/or any $C_{9+}$ aromatics in the first mixture are removed via line 303. The remainder is passed to the first separation stage 102. The amount of the one or more by-products removed in the separation stage 301 may be 5.0 to 100.0 wt. %, based on the amount of the by-product in the first mixture 101. The lower limit on the amount of by-product removed from the first mixture 101 may be 5.0 wt. %, 10.0 wt. %, 20.0 wt. %, 30.0 wt. %, 40.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, or 100.0 wt. %. The upper limit on the amount of by-product removed from the first mixture 101 may be 5.0 wt. %, 10.0 wt. %, 20.0 wt. %, 30.0 wt. %, 40.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, or 100.0 wt. %. Any combination of lower and upper limits on the amount of by-product removed from the first mixture 101 is expressed disclosed. In particular aspects, the by-product removed via line 303 is o-xylene. In another aspect, the by-product comprises one or more $C_{9+}$ aromatic compounds. In particular aspects, the portion of the $C_{8+}$ hydrocarbons provided to stage 301, e.g., via line 204, comprises ≥50.0 wt. %, ≥55.0 wt. %, ≥60.0 wt. %, ≥65.0 wt.

%, ≥70.0 wt. %, ≥75.0 wt. %, ≥80.0 wt. %, ≥85.0 wt. %, ≥90.0 wt. %, ≥95.0 wt. %, ≥99.0 wt. %, p-xylene. Optional fourth separation stage will now be described in more detail.

Fourth separation stage 304 may be any suitable separation means, e.g., distillation tower, stabilization tower, flash drum, etc. At least a portion of the reactor effluent comprising the $C_{8+}$ hydrocarbons separated in second separation stage 201 via line 203 may be provided to fourth separation stage 304, for removing and conducting away from the process at least a portion of one or more of toluene, o-xylene or $C_{9+}$ aromatics. A p-xylene containing portion exits third separation stage 304 via a stream 306, which may be further processed or purified. In particular aspects at least a portion of p-xylene containing stream 306 may be recycled as described for streams 203 and 204.

Figure 4:
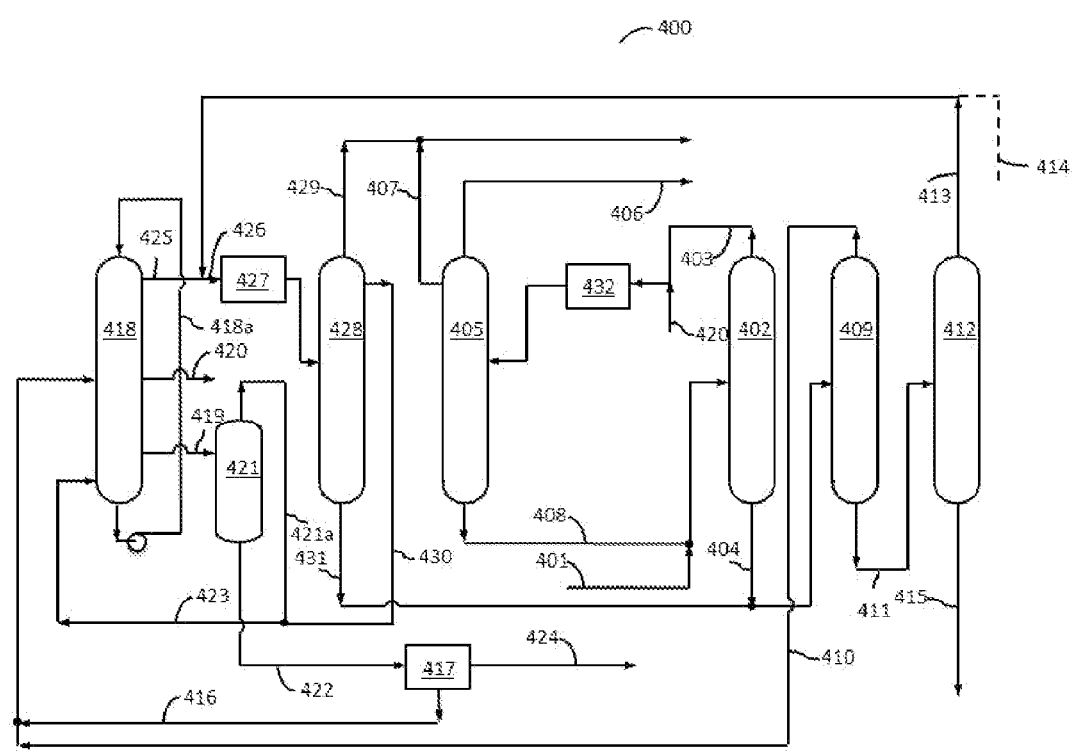
FIG. 4 illustrates another aspect of a p-xylene separation process according to the invention.

FIG. 4 illustrates a process 400 encompassing aspects of the invention. First mixture 401, comprising ethylbenzene, p-xylene, m-xylene, and o-xylene may be provided to optional distillation column 402. Optional distillation column 402 separates an ethylbenzene containing distillate 403 comprising p-xylene and m-xylene and a residue 404 comprising xylenes and a minor amount of ethylbenzene. In particular aspects, however, distillation tower 402 may be absent. In certain aspects where distillation column 402 is absent, first mixture 401 may be provided directly to distillation tower 409 or to first simulated moving bed absorptive separation column 418.

In aspects utilizing distillation tower 402, residue 404 is provided to distillation tower 409. Optional distillation tower 409 may be any separation means suitable for at least partially separating o-xylene from the residue 404. In particular aspects, distillation tower 409 may be a xylene splitter. Optionally, residue 404 may be combined with isomerate from isomerization reactor 427 described below.

Distillation tower 409 delivers a distillate through a line 410 comprising an increased concentration of the m-xylene and p-xylene, based on the concentration of these compounds as provided to the distillation tower 409. A residue comprising o-xylene exits the distillation tower 409 via line 411.

The o-xylene in line 411 is further isolated in a distillation column 412 from which o-xylene-containing distillate is removed from line 413. At least a portion of the o-xylene exiting the distillation tower 412 via line 413 may be recycled to an isomerization reactor 427 or carried away from the process for further isolation or processing. A residue containing $C_{9+}$ hydrocarbons exits distillation tower 409 via line 415.

Distillate is provided to a first simulated moving bed absorptive separation column 418 having a desorbent, e.g., toluene, introduced therein from an external source (not shown) and recycled through column 418 via line 418a. A p-xylene containing portion is typically withdrawn along with desorbent via line 419. The p-xylene in line 419 may be directed to a distillation column 421 to separate the desorbent as a distillate fraction which is combined via line 421a with the desorbent in line 423 for recycle to stage 418. The p-xylene recovered as residue by line 422 generally has a high purity, e.g., 99.8%, or otherwise purified in at least one crystallization zone 417 at high temperature, as described European Patent EP-B-531 191, incorporated herein by reference in its entirety. The p-xylene conducted away via line 424 generally has a purity greater than 99.9%, for example. A liquid stream obtained from crystallization zone 417 can be withdrawn via line 416, combined the xylene-containing distillate in line 410 and provided to the first simulated moving bed absorptive separation stage 418.

An ethylbenzene-containing portion as described above is withdrawn from the column 418 via line 420, and is preferably removed from the process. Non-aromatics can be removed in stage 418 and conducted away (not shown).

A p-xylene depleted raffinate as described above is withdrawn from the column 418 via line 425. This raffinate typically comprises toluene and m-xylene. The raffinate of line 425 is combined with the o-xylene-rich line 413, and introduced into isomerization reactor 427 via line 426. In particular aspects the p-xylene depleted raffinate in line 426 comprises <10 wt. % ethylbenzene and >10 wt. % toluene, based on the total weight of the components in line 426.

Isomerization reactor 427 may be any suitable reactor for isomerizing xylene/ethylbenzene mixtures. In particular aspects, the reactor 427 comprises a liquid phase isomerization process including a fixed bed of a zeolitic catalyst such as ZSM-5, under isomerization conditions the increase the content of p-xylene therein, preferably operated in the absence of hydrogen at a space velocity of 3 $hr^{-1}$, for example, at a temperature of about 260° C. and a pressure <30 bar.

This reactor effluent exits the reactor 427 and is introduced into a distillation column 428 (for example a distillation column comprising about 30 plates). Distillation column 428 separates the reactor effluent into a light fraction (e.g., $C_1$-$C_7$ hydrocarbon, particularly $C_1$-$C_7$ non-aromatic hydrocarbon) recovered by a line 429, a toluene fraction recycled by a line 430 to the adsorption column 418, and a xylene-enriched raffinate that is provided to distillation tower 409 via line 431. Optionally, residue 404 may be combined with distilled isomerate from the isomerization reactor 427.

Typically, the xylene-enriched raffinate 431 comprises p-xlene as the major isomer. A typical concentration of xylene isomers corresponding comprises 15 to 30 wt. % p-xylene, 10 to 30 wt. % o-xylene and 40 to 60 wt. % m-xylene. Typically, ethylbenzine comprises about 10 wt. % of the xylene-enriched raffinate.

Optionally, distillate 403 comprising p-xylene and m-xylene from the distillation column 402 may be fed, optionally in combination with ethylbenzene provided via line 420, to a catalytic vapor-phase isomerization reactor 432 of operating e.g., at a temperature of about 370-400° C. In aspects utilizing line 420, ethylbenzene conveyed via line 420 can be obtained from an external source (not shown). Typically, the distillate 403 comprises ≤10.0 wt. %, e.g., ≤7.5.0 wt. %, ≤5.0 wt. %, ≤2.5 wt. %, ≤1.0 wt. %, of the aromatic $C_8$ isomers in the xylene loop, based on the weight of aromatic $C_8$ isomers in the xylene loop. The resulting isomerate conducted away from stage 432 is enriched in xylene, and may be passed to separation stage 405. Light hydrocarbons i.e., $C_1$-$C_7$ hydrocarbons are separated and carried away form the process via line 407, optionally combined with the light hydrocarbons of line 429. Benzene and toluene may be separated from the isomerate, and optionally carried away from the process, via line 406. Isomerization effluent exits the separation stage 405 may be combined with the first mixture 401 and provided to the distillation column 402.

Particular Aspects

Additionally or alternatively, the present invention can include one or more of the following embodiments. The invention is not limited to these embodiments, and this description is not meant to foreclose other embodiments within the broader scope of the invention.

Embodiment 1. A process for producing p-xylene, the process comprising, (a) providing a first mixture comprising ≥5.0 wt. % of aromatic $C_8$ isomers, based on the weight of the first mixture, said $C_8$ isomers comprising p-xylene and ethylbenzene; (b) separating from the first mixture in a first separation stage one or more of (i) a p-xylene-containing portion, (ii) a non-aromatics containing portion, and (iii) an ethylbenzene-containing portion, to form a p-xylene-depleted raffinate, wherein the first separation stage includes at least one simulated moving-bed adsorptive separation stage; (c) reacting at least a portion the p-xylene-depleted raffinate in the liquid phase to produce a reactor effluent comprising aromatic $C_8$ isomers; and (d) combining with the first mixture ≥50.0 wt. %, preferably ≥90.0 wt. %, of the reactor effluent's aromatic $C_8$ isomers, preferably p-xylene, based on the weight of the reactor effluent's aromatic $C_8$ isomers, the combining being carried out before and/or during the separating of (b).

Embodiment 2. The process of Embodiment 1, wherein the separating step (b) includes separating from the first mixture: (A) the p-xylene-depleted raffinate; (B) the p-xylene-containing portion comprising ≥10.0 wt. % of the first mixture's p-xylene, based on the weight of the first mixture's p-xylene; and (C) the ethylbenzene-containing portion comprising ≥10.0 wt. % of the first mixture's ethylbenzene, based on the weight of the first mixture's ethylbenzene.

Embodiment 3. The process of Embodiment 1 or 2, further including conducting away at least a portion of the p-xylene-containing portion.

Embodiment 4. The process of any of Embodiments 1 to 3, further including conducting away ≥50.0 wt. % of the ethylbenzene-containing portion, based on the weight of the separated ethylbenzene.

Embodiment 5. The process of any of Embodiments 1 to 4, wherein the first mixture comprises ≥50.0 wt. % of a mixture of p-xylene, ethylbenzene, m-xylene, and o-xylene, based on the weight of the first mixture.

Embodiment 6. The process of any of Embodiments 1 to 5, wherein the first mixture comprises about 12 wt. % to 32 wt. %, particularly 17 wt. % to 27 wt. % or 20.0 wt. % to 25.0 wt. %, p-xylene; 35 wt. % to 55 wt. %, particularly 40 wt. % to 50 wt. % or 42.5 wt. % to 47.7 wt. %, m-xylene; 13 wt. % to 33 wt. %, particularly 18 wt. % to 28 wt. % or 20.0 wt. % to 25.0 wt. % o-xylene; and 1.0 wt. % to 20.0 wt. %, particularly 5.0 wt. % to 15.0 wt. % or 7.5 wt. % to 12.5 wt. %, ethylbenzene.

Embodiment 7. The process of any of Embodiments 1 to 6, wherein reacting at least a portion the p-xylene-depleted raffinate in the liquid phase includes at least one of (i) one or more reforming reactions, (ii) one or more disproportionation reactions, (iii) one or more transalkylation reactions, and (iv) one or more cracking reactions.

Embodiment 8. The process of any of the Embodiments encompassed by Embodiment 7, further comprising: (e) separating from the reactor effluent in a second separation stage at least a portion of any $C_1$-$C_7$ compounds produced during the reacting step (c), the step (e) being carried out before the combining step (d); and (f) conducting the separated $C_7$ compounds away from the process.

Embodiment 9. The process of any of Embodiments 1 to 8, wherein the process further comprises: (g) removing a by-product from the first mixture, the by-product comprising (1) at least a portion of the first mixture's o-xylene and/or (2) at least a portion of any $C_{9+}$ aromatics in the first mixture; and/or (h) separating from the reactor effluent in a third separation stage one or more of toluene, o-xylene or $C_{9+}$ aromatics, and conducting away at least a portion of one or more of the separated toluene, the separated o-xylene, and the separated $C_{9+}$ aromatics.

Embodiment 10. The process of any of the Embodiments encompassed by Embodiment 9, further comprising separating from the first mixture in the first separation stage ≥50.0 wt. %, preferably ≥75.0 wt. %, or ≥90.0 wt. %, of any non-aromatic hydrocarbon molecules.

Embodiment 11. The process of any of Embodiments 1-10, wherein the reacting of step (c) includes liquid-phase isomerization, and wherein ≤10.0 wt. % of the p-xylene-depleted raffinate is in the vapor phase during the reacting, the weight percent being based on the weight of the p-xylene-depleted raffinate.

Embodiment 12. The process of Embodiment 11, wherein ≤1.0 wt. %, preferably ≤0.1 wt. %, of the p-xylene-depleted raffinate is in the vapor phase during the reacting.

Embodiment 13. The process of any of Embodiments 1-12, wherein (i) ≥90.0 wt. % of the first mixture's ethylbenzene is separated by chromatographic separation in the first separation stage, (ii) ≥90.0 wt. % of the separated ethylbenzene is conducted away from the process, and (iii) ≥90.0 wt. % of the reactor effluent's aromatic $C_8$ isomers are combined with the first mixture in step (d).

Embodiment 14. In a xylene loop, wherein the xylene loop comprises (a) providing a first mixture comprising aromatic $C_8$ isomers; (b) separating from the first mixture in a first stage: (i) a p-xylene-depleted raffinate; (ii) a p-xylene-containing portion comprising ≥10.0 wt. % of the mixture's p-xylene, based on the weight of the mixture's p-xylene; and at least one of (iii) an ethylbenzene-containing portion comprising ≥10.0 wt. % of the first mixture's ethylbenzene, based on the weight of the first mixture's ethylbenzene; or (iv) ≥10.0 wt. % of any non-aromatics in the first mixture; wherein the first separation stage includes at least one simulated moving-bed adsorption chromatographic separation; (c) conducting away at least a portion of the separated p-xylene; (d) reacting at least a portion the p-xylene-depleted raffinate in the liquid phase to produce a reactor effluent comprising aromatic $C_8$ isomers; and (e) recycling to step (b) ≥50.0 wt. % of aromatic $C_8$ isomers of the reactor effluent, based on the weight of the aromatic $C_8$ isomers in the reactor effluent; the improvement comprising: (f) conducting away from the xylene loop (i) ≥50.0 wt. % of the ethylbenzene separated in step (c), based on the weight of the separated ethylbenzene, and/or (ii) ≥50.0 wt. % of any non-aromatics separated in step (c); and (g) exposing ≤10.0 wt. % of aromatic $C_8$ isomers in the xylene loop to vapor-phase isomerization, based on the weight of aromatic $C_8$ isomers in the xylene loop.

Embodiment 15. The process of Embodiment 14, wherein the first mixture comprises ≥50.0 wt. % of a mixture of p-xylene, ethylbenzene, m-xylene, and o-xylene, based on the weight of the first mixture.

Embodiment 16. The process of Embodiment 14 or 15, wherein the first mixture comprises about 12 wt. % to 32 wt. %, particularly 17 wt. % to 27 wt. % or 20.0 wt. % to 25.0 wt. %, p-xylene; 35 wt. % to 55 wt. %, particularly 40 wt. % to 50 wt. % or 42.5 wt. % to 47.7 wt. %, m-xylene; 13 wt. % to 33 wt. %, particularly 18 wt. % 28 wt. %, or 20.0 wt. % to 25.0 wt. % o-xylene; and 1.0 wt. % to 20.0 wt. %, particularly 5.0 wt. % to 15.0 wt. % or 7.5 wt. % to 12.5 wt. %, ethylbenzene.

Embodiment 17. The process of any of Embodiments 14 to 16, wherein reacting at least a portion the p-xylene-depleted raffinate in the liquid phase includes at least one of (i) one or more reforming reactions, (ii) one or more disproportionation reactions, (iii) one or more transalkylation reactions, and (iv) one or more cracking reactions.

Embodiment 18. The process of any of Embodiments 14 to 17, further comprising: (h) separating from the reactor effluent in a second separation stage at least a portion of any $C_1$-$C_7$ compounds produced during the reacting step (c), the step (e) being carried out before the combining step (d); and (i) conducting the separated $C_1$-$C_7$ compounds away from the process.

Embodiment 19. The process of any of Embodiments 14 to 18, wherein the process further comprises: (j) removing a by-product from the first mixture, the by-product comprising (1) at least a portion of the first mixture's o-xylene and/or (2) at least a portion of any $C_{9+}$ aromatics in the first mixture; and/or (k) separating from the reactor effluent in a third separation stage one or more of toluene, o-xylene or $C_{9+}$ aromatics, and conducting away at least a portion of one or more of the separated toluene, the separated o-xylene, and the separated $C_{9+}$ aromatics.

Embodiment 20. The process of any embodiment encompassed by Embodiment 19, further comprising separating from the first mixture in the first separation stage ≥50.0 wt. %, preferably ≥75.0 wt. %, or ≥90.0 wt. %, of any non-aromatic hydrocarbon molecules.

Embodiment 21. The process of any of Embodiments 14 to 20, wherein the reacting of step (d) includes liquid-phase isomerization, and wherein ≤10.0 wt. % of the p-xylene-depleted raffinate is in the vapor phase during the reacting, the weight percent being based on the weight of the p-xylene-depleted raffinate.

Embodiment 22. The process of any embodiment encompassed by Embodiment 20, wherein ≤1.0 wt. %, preferably ≤0.1 wt. %, of the p-xylene-depleted raffinate is in the vapor phase during the reacting.

Embodiment 23. The process of any of Embodiments 14 to 22, wherein (i) ≥90.0 wt. % of the first mixture's ethylbenzene is separated by chromatographic separation in the first separation stage, (ii) ≥90.0 wt. % of the separated ethylbenzene is conducted away from the process, and (iii) ≥90.0 wt. % of the reactor effluent's aromatic $C_8$ isomers are combined with the first mixture in step (d).

Embodiment 24. A process for producing p-xylene, the process comprising, (a) providing a first mixture comprising ≥5.0 wt. % of aromatic $C_8$ isomers, based on the weight of the first mixture, said $C_8$ isomers comprising p-xylene and ethylbenzene; (b) separating from the first mixture in a first separation stage wherein the first separation stage includes at least one simulated moving-bed adsorptive separation stage: (i) a p-xylene-depleted raffinate; (ii) a p-xylene-containing portion comprising ≥10.0 wt. % of the first mixture's p-xylene, based on the weight of the first mixture's p-xylene; and (iii) an ethylbenzene-containing portion comprising ≥10.0 wt. % of the first mixture's ethylbenzene, based on the weight of the first mixture's ethylbenzene; (c) conducting away at least a portion of the p-xylene-containing portion; (d) conducting away ≥50.0 wt. % of the ethylbenzene-containing portion, based on the weight of the ethylbenzene-containing portion; (e) isomerizing at least a portion the p-xylene-depleted raffinate in the liquid phase wherein ≤10.0 wt. %, e.g., ≤1.0 wt. % or 0.1 wt. %, of the p-xylene-depleted raffinate is in the vapor phase during the isomerizing, the weight percent being based on the weight of the p-xylene-depleted raffinate, to produce a reactor effluent comprising ≥90.0 wt. % p-xylene, based on the weight of the reactor effluent's aromatic $C_8$ isomers; and (f) combining with the first mixture at least a portion of the reactor effluent, the combining being carried out before and/or during the separating of (b).

Embodiment 25. The process of Embodiment 24, further comprising: (g) removing a by-product from the first mixture, the by-product comprising (1) at least a portion of the first mixture's o-xylene and/or (2) at least a portion of any $C_{9+}$ aromatics in the first mixture; and/or (h) separating from the reactor effluent in a third separation stage one or more of toluene, o-xylene or $C_{9+}$ aromatics, and conducting away at least a portion of one or more of the separated toluene, the separated o-xylene, and the separated $C_{9+}$ aromatics; and wherein step (b) further includes (iv) a non-aromatic hydrocarbon portion, comprising ≥50.0 wt. %, preferably ≥75.0 wt. %, or ≥90.0 wt. %, of the first mixture's non-aromatic hydrocarbon molecules.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the enforceable scope of the present invention.

As demonstrated above, aspects of the invention provide methods of making p-xylene, particularly in a xylene loop. The new methods have one or more of the following advantages. For example, the vapor-phase isomerization stage may be further reduced in size when non-aromatics are separated and conducted away from the xylene loop upstream of isomerization. Vapor-phase isomerization stage(s) can be eliminated altogether when substantially all of the non-aromatics and substantially all of the ethylbenzene are separated and conducted away from the xylene loop upstream of isomerization. An advantage of some aspects is that the same type of chromatographic separation as is used for p-xylene and ethylbenzene separation from a mixture of aromatic $C_8$ isomers can also be utilized for separating and removing non-aromatics from the loop, e.g., as a component of a third raffinate, upstream of the isomerization stage. In the conventional process, vapor-phase isomerization is needed for cracking these molecules into lower molecular weight fragments. The invention overcomes this difficulty because the sufficient non-aromatics are conducted away from the xylene loop as a component of the third raffinate. Other characteristics and additional advantages are apparent to those skilled in the art.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including". Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for producing p-xylene, the process comprising:
(a) providing a first mixture comprising aromatic $C_8$ isomers;

(b) separating from the first mixture in a first stage:
   (i) a p-xylene-depleted raffinate;
   (ii) a p-xylene-containing portion comprising ≥10.0 wt. % of the mixture's p-xylene; and
   (iii) an ethylbenzene-containing portion comprising ≥10.0 wt. % of the mixture's ethylbenzene; wherein the first separation stage includes at least one simulated moving-bed adsorption chromatographic separation;
(c) conducting away at least a portion of the separated p-xylene;
(d) reacting at least a portion of the p-xylene-depleted raffinate in the liquid phase to produce a first reactor effluent comprising aromatic $C_8$ isomers;
(e) separating from the first reactor effluent in a second separation stage a toluene-containing fraction and a xylene-enriched raffinate;
(f) separating from the xylene-enriched raffinate an o-xylene-containing distillate;
(g) recycling at least a portion of the o-xylene-containing distillate directly to the reacting in (d);
(h) conducting away ≥50.0 wt. % of the ethylbenzene separated in (b)(iii); and
(i) exposing ≤10.0 wt. % of aromatic $C_8$ isomers in the process to vapor-phase isomerization to produce a second reactor effluent comprising aromatic $C_8$ isomers.

2. The process of claim 1, wherein the first mixture comprises ≥50.0 wt. % of a mixture of p-xylene, ethylbenzene, m-xylene, and o-xylene.

3. The process of claim 1, wherein the first mixture comprises about 17 wt. % to 27 wt. % p-xylene, 40 wt. % to 50 wt. % m-xylene, 18 wt. % to 28 wt. % o-xylene, and 5 wt. % to 15 wt. % ethylbenzene.

4. The process of claim 1, wherein reacting at least a portion the p-xylene-depleted raffinate in the liquid phase includes one or more transalkylation reactions.

5. The process of claim 1, further comprising:
(j) separating from the first reactor effluent in the second separation stage at least a portion of any $C_1$-$C_7$ compounds produced during the reacting in (d); and
(k) conducting the separated $C_1$-$C_7$ compounds away from the process.

6. The process of claim 1, further comprising separating from the first mixture in the first separation stage ≥50.0 wt. % of any non-aromatic hydrocarbon molecules.

7. The process of claim 1, wherein the reacting in (d) includes liquid-phase isomerization, and wherein ≤10.0 wt. % of the p-xylene-depleted raffinate is in the vapor phase during the reacting.

8. The process of claim 1, wherein ≤1.0 wt. % of the p-xylene-depleted raffinate is in the vapor phase during the reacting.

9. The process of claim 1, wherein (i) ≥90.0 wt. % of the first mixture's ethylbenzene is separated by chromatographic separation in the first separation stage, (ii) ≥90.0 wt. % of the separated ethylbenzene is conducted away from the process, and (iii) ≥90.0 wt. % of the reactor effluent's aromatic $C_8$ isomers are combined with the first mixture in step (d).

10. The process of claim 1,
wherein the p-xylene-containing portion further comprises a desorbent from the separating in (b);
wherein the process further comprises:
   (l) separating from the p-xylene containing portion a distillate fraction comprising the desorbent; and
   (m) recycling the distillate fraction to the separating in (b).

11. The process of claim 10, further comprising:
(n) separating from the p-xylene-containing portion a residue comprising p-xylene during the separating in (l); and
(o) concentrating a p-xylene content of the residue in a crystallization zone to produce a concentrated p-xylene stream and a liquid stream;
(p) recycling the liquid stream to the separating in (b).

* * * * *